(12) United States Patent
Andriacchi et al.

(10) Patent No.: US 11,576,807 B2
(45) Date of Patent: *Feb. 14, 2023

(54) METHOD OF TREATING PAIN

(71) Applicant: The Board of Trustees of the Leland Stanford Junior University, Stanford, CA (US)

(72) Inventors: Thomas P. Andriacchi, Zephyr Cove, NV (US); Jennifer C. Erhart-Hledik, Menlo Park, CA (US)

(73) Assignees: The United States Government as Represented by the Department of Veterans Affairs, Washington, DC (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/211,023

(22) Filed: Mar. 24, 2021

(65) Prior Publication Data

US 2021/0205116 A1 Jul. 8, 2021

Related U.S. Application Data

(63) Continuation of application No. 15/561,012, filed as application No. PCT/US2016/027849 on Apr. 15, 2016, now Pat. No. 11,285,034.

(Continued)

(51) Int. Cl.
*A61F 5/30* (2006.01)
*A61F 7/00* (2006.01)
(Continued)

(52) U.S. Cl.
CPC ............... *A61F 5/30* (2013.01); *A61F 7/00* (2013.01); *A61F 2007/0039* (2013.01);
(Continued)

(58) Field of Classification Search
CPC .......... A61H 7/00; A61H 7/002; A61H 7/003; A61H 7/004; A61H 7/005; A61H 7/007;
(Continued)

(56) References Cited

U.S. PATENT DOCUMENTS 3,323,517 A    6/1967   Keller
4,989,605 A    2/1991   Rossen
(Continued)

OTHER PUBLICATIONS

Becker et al. "Neuromuscular quadriceps dysfunction prior to osteoarthritis of the knee," Journal of Orthopaedic Research, vol. 22, 2004, pp. 768-773.
(Continued)

*Primary Examiner* — Colin W Stuart
*Assistant Examiner* — Matthew D Ziegler
(74) *Attorney, Agent, or Firm* — Peter W. Schroen; Bret E. Field; Bozicevic, Field & Francis LLP

(57) ABSTRACT

Aspects of the cutaneous stimulation devices include a cutaneous stimulation module and a cutaneous association element configured to stably associate the module with a skin location. The cutaneous stimulation module may be an active or passive module. Also provided are methods of using the devices, e.g., in rehabilitation and/or pain mitigation applications.

13 Claims, 5 Drawing Sheets

Related U.S. Application Data

(60) Provisional application No. 62/147,896, filed on Apr. 15, 2015.

(51) Int. Cl.
*A61H 23/02* (2006.01)
*A61H 39/06* (2006.01)

(52) U.S. Cl.
CPC ...... *A61F 2007/0093* (2013.01); *A61H 23/02* (2013.01); *A61H 39/06* (2013.01); *A61H 2201/0207* (2013.01); *A61H 2201/164* (2013.01); *A61H 2201/165* (2013.01); *A61H 2201/5005* (2013.01); *A61H 2201/5064* (2013.01); *A61H 2201/5069* (2013.01); *A61H 2201/5071* (2013.01)

(58) Field of Classification Search
CPC .. A61H 11/00; A61H 11/02; A61H 2011/005; A61H 23/02; A61H 39/06; A61H 2201/0157; A61H 2201/02; A61H 2201/0207; A61H 2201/0214; A61H 2201/16; A61H 2201/164; A61H 2201/165; A61H 2201/50; A61H 2201/5005; A61H 2201/5058; A61H 2201/5064; A61H 2201/5069; A61H 2201/5071; A61H 2205/10–108; A61H 2207/00; A61F 5/30; A61F 7/00; A61F 2007/0039; A61F 2007/0093
See application file for complete search history.

(56) References Cited

U.S. PATENT DOCUMENTS

| | | | |
|---|---|---|---|
| 6,066,110 A * | 5/2000 | Nauert | A61F 5/0123 602/26 |
| 6,132,392 A | 10/2000 | Stone | |
| 6,273,863 B1 | 8/2001 | Avni et al. | |
| 6,487,906 B1 | 12/2002 | Hock | |
| 6,500,210 B1 | 12/2002 | Sabolich et al. | |
| 6,615,086 B2 | 9/2003 | Tsai | |
| 6,872,187 B1 | 3/2005 | Stark et al. | |
| 6,878,122 B2 | 4/2005 | Gordo | |
| 7,571,002 B2 | 8/2009 | Thorpe | |
| 8,740,825 B2 | 6/2014 | Ehrenreich et al. | |
| 8,928,484 B2 | 1/2015 | Chang et al. | |
| 9,311,789 B1 | 4/2016 | Gwin | |
| 9,452,101 B2 | 9/2016 | Tomlinson | |
| 9,616,234 B2 * | 4/2017 | Harry | A61N 2/006 |
| 9,943,461 B1 | 4/2018 | Muench | |
| 2002/0068886 A1 | 6/2002 | Lin | |
| 2004/0173220 A1 | 9/2004 | Harry et al. | |
| 2005/0131317 A1 | 6/2005 | Oddson | |
| 2006/0258962 A1 | 11/2006 | Koranic | |
| 2006/0258963 A1 | 11/2006 | Kopanic | |
| 2008/0077192 A1 | 3/2008 | Harry | |
| 2008/0086063 A1 | 4/2008 | Baxter | |
| 2011/0295165 A1 | 12/2011 | Cavallaro | |
| 2012/0046579 A1 | 2/2012 | Radi | |
| 2013/0012850 A1 | 1/2013 | Hutcheon | |
| 2013/0040835 A1 | 2/2013 | Harris | |
| 2013/0204169 A1 | 8/2013 | Poepperling | |
| 2013/0225954 A1 | 8/2013 | Ludlow et al. | |
| 2014/0261430 A1 | 9/2014 | Davis | |
| 2015/0005683 A1 | 1/2015 | Balducci | |
| 2015/0173993 A1 | 6/2015 | Walsh et al. | |
| 2016/0158097 A1 | 6/2016 | Harper | |
| 2016/0339240 A1 | 11/2016 | Mihara | |

OTHER PUBLICATIONS

Bodor et al. "Quadriceps protects the anterior cruciate ligament," Journal of Orthopaedic Research, vol. 19, 2001, pp. 629-633.

Childs et al. "Alterations in lower extremity movement and muscle activation patterns in individuals with knee osteoarthritis," Clinical Biomechanics, vol. 19, No. 1, Jan. 2004, pp. 44-49.

Deyo et al. "A Controlled Trial of Transcutaneous Electrical Nerve Stimulation (TENS) and Exercise for Chronic Low Back Pain", The New England Journal of Medicine, vol. 322, No. 23, Jun. 7, 1990, pp. 1627-1634.

Dooley, et al. "Regulation of gene expression in inflammatory bowel disease and correlation with IBD drugs: □creening by DNA microarrays", Inflamm Bowel Dis. Jan. 2004;10{1):1-14.

Dowling et al. "Gait Modification via Verbal Instruction and an Active Feedback System to Reduce Peak Knee Adduction Moment", Journal of Biomechanical Engineering, vol. 132, Jul. 2010, 071007-1-071007-5 (5 pages).

Erhart-Hledik et al. "Effects of Active Feedback Gait Retraining to Produce a Medial Weight Transfer at the Foot in Subjects With Symptomatic Medial Knee Osteoarthritis", Journal of Orthopaedic Research, vol. 35, No. 10, Oct. 2017, pp. 2251-2259.

Fisher et al. "The therapeutic potential for changing patterns of locomotion: An application to the ACL deficient knee," 2003 Summer Bioengineering Conference, Jun. 25-29, 2003, Sonesta Beach Resort, Key Biscayne, Florida, 2 pages.

Fischer et al. "Activating the Somatosensory System Can Assist in Restoring Quadriceps Function during Gait", Orthopaedic Research Society (ORS) 2017 Annual Meeting, San Diego, CA, Mar. 19-22, 2017, Poster No. 2404, 1 page.

Lewek et al. "The effect of insufficient quadriceps strength on gait after anterior cruciate ligament reconstruction," Clinical Biomechanics, vol. 17, No. 1, Jan. 2002, pp. 56-63.

Lewek et al. "Quadriceps femoris muscle weakness and activation failure in patients with symptomatic knee osteoarthritis," Journal of Orthopaedic Research, vol. 22, 2004, pp. 110-115.

Pietrosimone et al. "Effects of Disinhibitory Transcutaneous Electrical Nerve Stimulation and Therapeutic Exercise on Sagittal Plane Peak Knee Kinematics and Kinetics in People with Knee Osteoarthritis During Gait: A Randomized Controlled Trial", Clinical Rehabilitation, vol. 24, 2010, pp. 1091-1101.

Sluka et al. "Transcutaneous Electrical Nerve Stimulation: Basic Science Mechanisms and Clinical Effectiveness", The Journal of Pain, vol. 4, No. 3, Apr. 2003, pp. 109-121.

\* cited by examiner

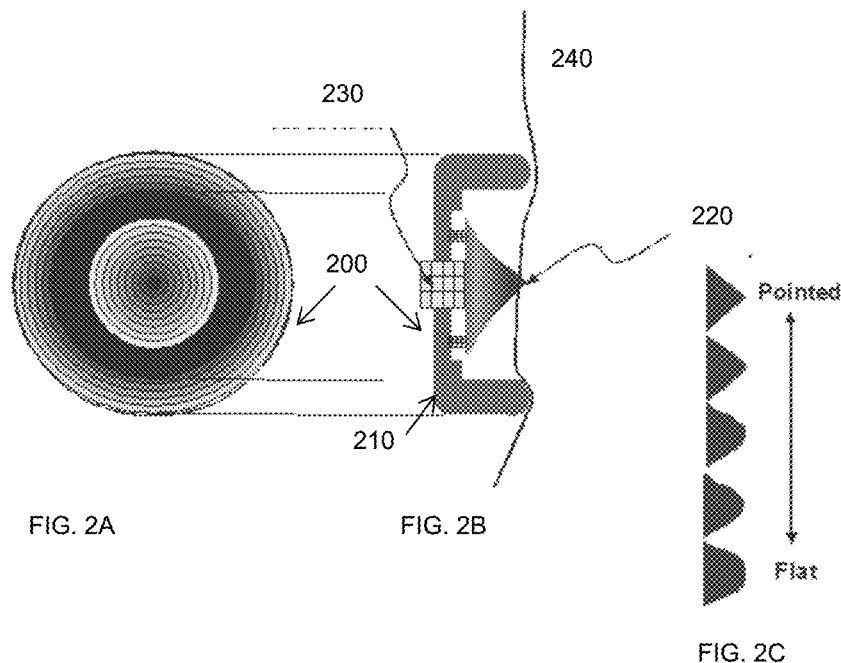
FIG. 2A  FIG. 2B
FIG. 2C
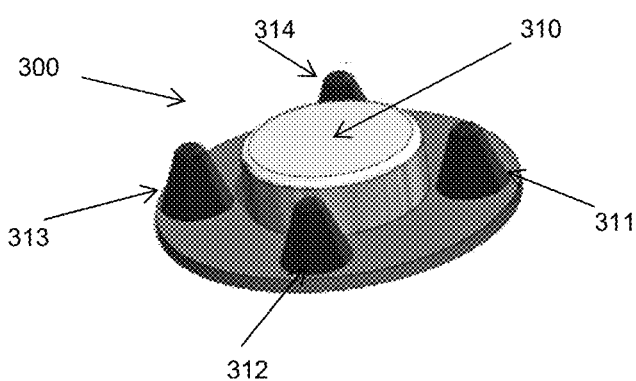
FIG. 3

METHOD OF TREATING PAIN

CROSS-REFERENCE TO RELATED APPLICATIONS

Pursuant to 35 U.S.C. § 119 (e), this application claims priority to the filing date of the U.S. Provisional Patent Application Ser. No. 62/147,896, filed Apr. 15, 2015; the disclosure of which is herein incorporated by reference.

INTRODUCTION

Physical therapy, braces, elastic wraps, electrical stimulation and taping have been commonly used to treat many types of musculoskeletal conditions. These treatments are thought to improve muscle strength, joint stability and mitigate pain. While these interventions have achieved some clinical success, it is often the case that the results are not sustained due to limitations associated with compliance in using the therapy or continuing to wear a particular intervention.

Neuromuscular dysfunction, such as decreased quadriceps muscle strength and voluntary activation, has been demonstrated in patients with osteoarthritis and with other joint pathologies, including ligament injuries and meniscectomy. Physical therapy, braces, elastic wraps, and taping have been commonly used to treat many types of these musculoskeletal conditions. For example, rehabilitative programs including quadriceps strengthening have been shown to reduce pain and disability in subjects with knee osteoarthritis. Quadriceps strengthening, however, may require complex clinic-based regimens or machinery not readily availability to patients, and can have poor adherence rates. Further, despite aggressive rehabilitation programs directed at improving quadriceps function following anterior cruciate ligament (ACL) injury and reconstruction, a condition leading to accelerated joint degeneration, a universally accepted effective treatment approach to reverse this muscle weakness has yet to be identified. The quadriceps weakness following ACL injury has been shown to be related to the potential for re-injury and development of knee osteoarthritis (OA). Thus while available interventions have achieved some clinical success, it is often the case that the results are not sustained due to limitations associated with compliance in using the therapy or continuing to the wear a particular intervention.

SUMMARY

Embodiments of the invention, e.g., as described below, offer a low cost alternative to existing treatments such as rehabilitation programs, elastic wraps, and bracing, with potential for improvements in function, pain, and reduced re-injury risk, with a highly favorable risk to benefit ratio.

Cutaneous stimulation devices are provided. Aspects of the devices include a cutaneous stimulation module and a cutaneous association element configured to stably associate the module with a skin location. The cutaneous stimulation module may be an active or passive module. Also provided are methods of using the devices, e.g., in rehabilitation and/or pain mitigation applications.

Embodiments of this invention address problems with existing devices by introducing a low profile device that can be easily applied, can be worn in an unobtrusive manner and can be constructed at a reasonable cost. In addition, there are features of embodiments of the invention that can be customized to the patient's specific needs and body type.

The devices and methods described herein find use in a variety of different applications, such as the treatment of musculoskeletal conditions, e.g., conditions associated with a joint, such as hip, ankle, knee, shoulder elbow, back, etc. One application of this invention involves the treatment of osteoarthritis (OA) of the knee. Knee OA is a prevalent condition that contributes significantly to functional limitations and disability, resulting in a significant burden on health care provision. Changes observed in individuals with knee OA include altered activity patterns of key lower extremity muscles involved in gait. Correct muscle activity is important not only for joint motion but also plays a crucial role in joint protection. While these alterations in muscle function in OA may be attempts to reduce pain and protect the knee from further degeneration, over the long term, an impairment in muscle activity may result in a change in mechanical stress loading of a joint and have adverse effects on the knee joint. Altered muscle activity has also been found to precede the onset of knee OA in populations at risk for development of the disease, such as following meniscectomy and anterior cruciate ligament (ACL) reconstruction surgery, and may be a factor not only in progression of the disease but also a factor in the pathogenesis of knee OA. Knee injuries and disease cause substantial pain and disability, and their high prevalence necessitate simple interventions. Clinical guidelines for management of knee OA and associated joint injuries emphasize the importance of non-pharmacological conservative strategies. Gait modification through cutaneous stimulation as provided by embodiments of the present invention offers a low cost alternative to rehabilitation programs and current treatments to address deficient muscle activation in knee OA and conditions related to development of the disease.

BRIEF DESCRIPTION OF THE FIGURES

FIGS. 2A-2C illustrate an active stimulus module according to an embodiment of the invention.

FIG. 3 shows a device according to an embodiment of the invention where the device includes both active and passive stimulus modules, arranged with a central active vibratory module surrounded circumferentially by four passive modules.

DETAILED DESCRIPTION

Figure 1:
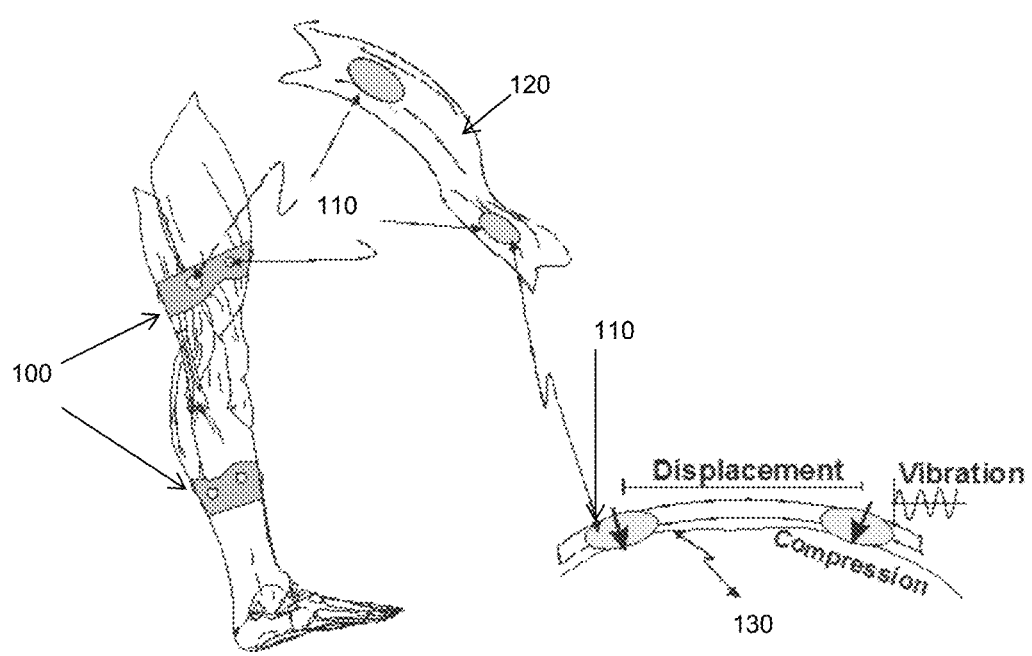
FIG. 1 shows a device according to an embodiment of the invention.

Cutaneous stimulation devices are provided. Aspects of the devices include a cutaneous stimulation module and a cutaneous association element configured to stably associate the module with a skin location. The cutaneous stimulation module may be an active or passive module. Also provided are methods of using the devices, e.g., in rehabilitation and/or pain mitigation applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges may be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which may be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Cutaneous Stimulation Devices

As summarized above, aspects of the invention include cutaneous stimulation devices. Cutaneous stimulation devices are devices configured to apply a stimulus to one or more skin locations, i.e., one or more topical or cutaneous locations, of a subject. Stimuli that may be imparted by the stimulation devices are ones that produce a tactile sensation in a cutaneous region operably coupled to the stimulation device, such that the stimulation modules are configured to apply a tactile stimulus, such as a mechanical or thermal stimulus, to the target skin location. The tactile sensation may be a mechanical sensation and/or a thermal sensation. Mechanical sensations include pressure sensations, e.g., resulting from a structure of the module pressing into a cutaneous region, resulting from a vibrating module, resulting from a displaced module, etc. Thermal sensations include hot or cold sensations, e.g., as imparted by a module having a temperature modulated, e.g., heated or cooled, skin contact surface, etc. In some instances, the stimulus that is imparted by the module is not an electrical stimulation, such that the stimulation device is not an electrostimulation device. As such, the nature of the stimulus that is imparted by the stimulator to the skin location may vary, where stimuli of interest include, but are not limited to: pressure, temporal displacement, vibration, thermal modulation, e.g., in the form of heat or cooling, etc.

The skin location to which the stimulation modules apply a stimulus may vary. The skin location may be any location of a body, such as a location at or proximal to a bone joint. Locations to which stimulation modules may be applied include, but are not limited to: knee locations, ankle locations, hip locations, elbow locations, wrist locations, shoulder locations, neck locations, back locations, etc. The particular location to which the stimulus module is applied will vary depending on the application and target bone/joint area. In some instances, a cutaneous region is proximal to a target bone/join area if it is 0.1 to 50 cm from that area, such as 0.2 to 20 cm from area, e.g., 0.5 to 10 cm from that area. In some instances the skin location is present on a limb, e.g., an arm or a leg. In some instances the skin location is associated with a knee location of a leg. By knee location is meant a location at or proximal to a knee. Where the location is proximal to a knee, the distance between the location and the knee may vary, ranging in some instances from 0.2 cm to 40 cm, such as 2 to 10 cm.

Aspects of the devices include a cutaneous stimulation module and a cutaneous association element configured to stably associate the module with a skin location. By cutaneous stimulation module is meant a structure or unit that is configured to impart a stimulus to a cutaneous area or region, e.g., as described above. As such, stimulation modules of interest include mechano-stimulatory modules, e.g., modules that apply pressure, vibrate, etc., thermal stimulatory modules, e.g., modules that change temperature to impart a thermal stimulation, such as a warm/hot or cool/cold sensation, etc.

Cutaneous stimulation modules of interest may assume a variety of different configurations, depending on their particular structure and type of stimulation that they are configured to impart. While the size of a given module may vary, e.g., depending on the particular application area, such as knee, hip, ankle, back, etc., in some instances the stimulation modules have a length ranging from 0.1 mm to 10 cm, such as 0.2 mm to 5 cm, e.g., 0.5 mm to 1 cm, a width ranging from 0.1 mm to 10 cm, such as 0.2 mm to 5 cm, e.g., 0.5 mm to 1 cm, and a height ranging from 0.1 mm to 10 cm, such as 0.2 mm to 5 cm, e.g., 0.5 mm to 1 cm.

A given stimulation module may be passive or active. In some instances, stimulation modules are passive stimulation modules. By passive stimulation module is meant a module that does not undergo a change to apply a cutaneous stimulus, e.g., does not change shape, temperature, vibrate, etc. Passive stimulation modules may be structures that, in combination with the cutaneous association element, apply a stimulus to a cutaneous region at desired time(s), e.g., in response to movement of the cutaneous region, etc. For example, devices that include passive stimulation modules may include an elastic band configured to encircle a portion of a limb of a subject; and a passive stimulation module stably associated with the elastic band and configured to apply pressure to a skin location in response to dimensional modulation, e.g., stretching, of the elastic band. In such embodiments, the stimulation modules may include a rigid skin contact surface. In such instances, the stimulation modules have a Mohs hardness sufficient to apply the desired pressure, where the Mohs hardness may range in some instances from 1.5 to 10, such as 2 to 8. Individual passive stimulation modules may have any convenient shape, including but not limited to spherical, conical, trapezoidal, cuboid, or irregular, where the modules may have rounded or sharp edges, as desired. The modules may be solid or hollow, and may be fabricated from any convenient material, including polymeric materials, metallic materials, etc. The dimensions of the modules may vary, so long as they are configured to apply the desired cutaneous stimulation. In some instances, the longest dimension of the modules ranges from 0.1 to 5 cm, such as 0.5 to 2.5 cm. The cutaneous stimulation modules may be fabricated using any convenient protocol, including three-dimensions (3D) printing protocols, which provides for customization of a given passive stimulation module for a particular patient, where desired.

Cutaneous stimulation modules may also be active stimulation modules. Active stimulation modules are modules that undergo a change in order to apply a desired cutaneous stimulus, e.g., they vibrate, they change temperature, they change shape, etc. Active stimulation modules that may be employed in devices of the invention may vary widely. For example, the active stimulation module may be configured to apply vibration, i.e., a vibratory force, to a skin location. While the stimulation module in such embodiments may vary, in some instances the module includes a vibratory element that is configured to vibrate at a frequency ranging from 20 to 450 Hz, such as 200 to 250 Hz. Alternatively or in addition to vibration, active stimulation modules may be configured to apply a thermal stimulus to a skin location of the subject, e.g., to apply heat or cold to the skin location. Embodiments of such modules include a skin contact surface that is configured to assume a desired temperature. While the desired temperature may vary, in some instances the temperature ranges from 5 to 45° C., such as 10 to 40° C. Alternatively, or in addition, the stimulation module may be configured to change shape so as to apply a desired mechanical stimulation, e.g., in the form of a pressure change, to a skin location. In such instances, the module may be configured to change a length of a dimension, such as the distance of skin contact surface extends beyond a module base, by a distance sufficient to produce the desired stimulus. While the magnitude of the change in length in such embodiments may vary, in some instances the magnitude ranges from 0.1 to 1 cm, such as 0.1 to 0.3 cm.

In some instances, devices of the invention or active stimulation modules thereof include a sensor configured to obtain physical data from the subject and output the obtained physical data to a processor; and a processor configured to activate the stimulator in response to received output physical data from the sensor.

In those embodiments where the device or cutaneous stimulation module thereof includes a sensor configured to obtain physical data from the subject and output the obtained physical data to a processor, the nature of the physical data that the sensor obtains may vary. Physical data that may be obtained or detected by the sensor include, but are not limited to: motion data, orientation data, e.g., knee flexion angle data, force data, etc. Any convenient sensor may be employed to obtain the desired physical data. Sensors of interest that may be incorporated into the cutaneous stimulus module include, but are not limited to: potentiometers, accelerometers, strain gauges, gyroscopes, flex sensors, pressure sensors, inertial measurement units, arthrometer (i.e., goniometer), etc.

As reviewed above, the cutaneous stimulation module may include a processing module configured to activate the stimulator in response to received output physical data from the sensor. For example, the processing module may be configured to receive the data from the sensor, determine a physiological parameter therefore if not already provided by the sensor as output, e.g., gait cycle, knee flexion angle, leg acceleration, etc., and then apply a stimulus as desired, e.g., a desired time during a gait cycle, when the knee is at a desired angle, etc. The processing module may vary based on the nature of the signal generated during specific phases of the movement where stimulus is needed. In general, the temporal variation of the signal from the sensor during specific movements provides the basis for activating the stimulus (where the processing module may be modified so as to be tailored to a given patient, e.g., via wired or wireless (e.g., from smart phone) protocol). The processing module may vary as desired and may be implemented as hardware, firmware, software or a combination thereof. The processing module may include any convenient processor.

As indicated above, the device or a cutaneous stimulation module thereof may include a sensor and a processor. As such, in such embodiments the sensor and processor may be present in the device as disparate components from the stimulation module(s). Alternatively, at least one of if not both of the sensor and processor may be integrated with a stimulation module, such that the stimulation module includes a stimulatory component and one or both of a sensor and processor, e.g., as described above. The connection between the disparate components may be wired or wireless, as desired.

Cutaneous stimulation modules may be stably associated with a cutaneous association element. By stably associated with is meant the module and the cutaneous association element are bound to each other in a manner such that they do not separate from each other during normal use, i.e., during use in the application for which they are designed. A cutaneous association element is an element or structure that is configured to provide for operational relationship between the stimulation module and the skin location, i.e., so that the module can impart the desired stimulus to the skin location. Examples of cutaneous association elements of interest include, but are not limited to: elastic bands, adhesives, e.g., where the adhesive is present on a skin association area of the cutaneous stimulation module or on a tape with which the cutaneous stimulus module is associated, etc.

As summarized above, aspects of the invention include cutaneous stimulation devices that include a cutaneous stimulation module stably associated with a cutaneous association element, e.g., an elastic band, a tape, etc. In some instances, the devices includes two or more, such as three or more, e.g., 4 or more cutaneous stimulation modules stably associated with the same a cutaneous association element, e.g., elastic band or adhesive tape, such that the cutaneous association element may be viewed as a connector for the stimulation modules. While the number of stimulation modules in such embodiments may vary, in some instances the number ranges from 2 to 50, such as 2 to 25, e.g., 3 to 20. In certain of these embodiments, the devices include at least one passive stimulation module and at least one active stimulation module, e.g., as described above. In these instances, the number of active and passive modules may be the same or may differ, e.g., where the device includes more passive modules than active modules. The arrangement of the multiple modules may also vary as desired, where examples of different arrangements that may be employed include linear arrangements, circumferential arrangements (e.g., where a central active module is surrounded by passive modules, such as illustrated in FIG. 3, below), etc.

Various aspects of the devices and components thereof, e.g., stimulations modules, have been generally described above, certain embodiments are now described in connection with the figures. As reviewed above, embodiments of the invention may be configured to provide an intervention that can be applied to the limb through, e.g., via an elastic brace, adhesive taping, or directly using an adhesive. An embodiment of a device according to an embodiment of the invention is illustrated in FIG. 1. The device 100 illustrated in FIG. 1 takes the form of an elastic band 120 with which two or more stimulus modules 110 are stably associated. During use, the elastic band 120 encircles a leg as shown, and movement of the leg results in application of a direct mechanical stimulus to the surface 130 of the skin (cutaneous stimulus) in the form of a static compressive pressure, a temporal displacement, an active vibration, or a thermal change that may also linked to the movement of the limb, as desired. As illustrated in FIG. 1, the elements of the invention include an elastic substrate 120 and a collection of strategically-placed stimulus modules 110. The stimulus modules can apply direct pressure to the surface of the skin and/or displace relative to an adjacent module when muscles contract or in response to inertial forces generated during movement. In addition, the module can contain a vibrator motor, e.g., as illustrated in FIG. 3 (described below) or thermal component that is activated/de-activated by movement.

FIGS. 2A-2C provide depictions of an active stimulation module according to embodiments of the invention, where the module includes a sensor, a stimulation component and a processor configured to activate the stimulation component in response to data obtained from the sensor. As illustrated in FIGS. 2A and 2B which provide bottom and lateral cross-sectional views of active stimulation module 200, the stimulus module 200 can create a tactile sensation that is sensed by the limb of the user. The module 200 includes a housing 210 and a shape adjustable skin contact element 220. As shown in FIG. 2C, the shape adjustable skin contact element 220 is configured to assume a number of different skin contact shapes or profiles, ranging from pointed to rounded. In addition, the module 200 includes an activator 230 which is configured change the shape of adjustable skin contact element 220. Where desired, activator 230 may further include a vibratory element to apply vibration to a location of a skin surface 240 and/or a thermal component to apply temperature modulation, e.g., in the form of heat or cold, to a location of skin surface 240. Module 200 includes a sensor to detect a motion/orientation/force, a processor to analyze said signal, and the activator 230 to produce a cutaneous stimulus. The shape of the cutaneous stimulus module at the skin surface can be adjusted, as shown in FIG. 2C. The stimulus module creates a tactile sensation that is sensed by the limb of the user, through cutaneous stimulation as shown in FIG. 2B. The module contains sensors (not shown) to detect the positioning and movement of the limb, producing a data signal indicative of the orientation of and/or inertial force generated by the limb. A microprocessor (not shown) embedded in the module uses the data signal from the sensors to produce a set of commands as a function of the data signal and triggers an activator within the stimulus module to produce a tactile stimulation to the skin surface. The shape of the cutaneous stimulus provided at the skin surface can be adjusted, as shown in FIG. 2C.

Devices as described herein may be designed to activate the mechanoreceptors of the somatosensory system to respond to a mechanical stimulus in a manner that elicits a functional response. As such, aspects of the invention include methods of activating the somatosensory system of a subject, e.g., to achieve a desired response, such as a therapeutic response. The somatosensory system controls the pain response, touch sensation and proprioception of an individual. The cross modal plasticity of this system can be exploited to induce desired changes in patterns of muscle contraction during common activities such as walking. An extreme example is a common limp (proprioception change) that results from joint pain. The skin has nerve endings that respond to stimuli in the form of displacement along the surface, compressive pressure and vibration. While the response to a constant stimulus can diminish, an intermittent stimulus will continue to produce a response. Thus one manifestation of this invention includes intermittent stimuli, e.g., a desired times, such as desired times during the gait cycle.

Methods

As summarized above, embodiments of the invention further include methods of applying a stimulus to a skin location of a subject. Aspects of such methods include stably associating a cutaneous stimulus module, e.g., as described above, with a target skin location, e.g., a location of a limb, such as a leg, and maintaining the stably associated cutaneous stimulus module with the skin location in a manner sufficient to apply a stimulus to the skin location. The manner may vary depending on whether the module is passive or active, e.g., as described above.

The duration that the device is applied to the subject may vary, and will be chosen to provide for the desired outcome. In some instances, the duration ranges from 6 hours to 1 year, such as 1 day to 6 months, e.g., 1 week to 3 months.

The devices and methods described here find use with a variety of different mammals. The terms "mammal" and "mammals" are used broadly herein to describe organisms which are within the class mammalia, including the orders carnivore (e.g., dogs and cats), rodentia (e.g., mice, guinea pigs, and rats), and primates (e.g., humans, chimpanzees, and monkeys). Mammals may be subjects or patients, such as human subjects or patients. The terms "human" or "humans" may include human subjects or patients of both genders and at any stage of development (i.e., fetal, neonates, infant, juvenile, adolescent, adult), where in certain embodiments the human subject is a juvenile, adolescent or adult. While the systems, devices and methods described herein may be applied on a human subject, it is to be understood that the subject systems, devices and methods may also be applied on other subjects (that is, in "non-human subjects").

Aspects of the invention further include methods of treating a subject for a condition. By treating or treatment is meant at least an amelioration of one or more symptoms associated with the condition, e.g., as described below, afflicting the subject, where amelioration is used in a broad sense to refer to at least a reduction in the magnitude of a parameter, e.g., symptom, associated with the pathological condition being treated, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition.

In some aspects of the subject methods, the method further comprises the step of measuring a parameter of the subject, such as symptom of the disease condition, a surrogate marker thereof, etc., to evaluate effectiveness of treatment. In some embodiments, the subject methods further include diagnosing an individual as having a condition that may be treated by the methods and devices of the invention.

Utility

Devices and methods of using the same in accordance with the invention can be used for a variety of rehabilitation purposes, due to its adaptability, in terms of placement of the device on the lower extremities and timing of the active stimulus module component of the device. Applications for this invention include, but are not limited to, rehabilitation for altered muscle activity due to injury or disease, as in individuals with knee osteoarthritis, ligamentous injuries (e.g., ACL injury), and degenerative joint conditions or surgical procedures such as meniscectomy or ACL reconstruction. While the devices and methods may be used for the treatment of a variety of different musculoskeletal conditions, examples of such conditions are conditions associated with movement of a bone joint, such as but not limited to: knee, ankle, hip, elbow, wrist, shoulder, neck, back, etc. Devices and methods as described herein find use in enhancing rehabilitation, e.g., by restoring strength through simulating muscle function during ambulation. Devices and methods according to embodiments of the invention provide a method to enhance muscle rehabilitation.

Applications of the devices and methods, e.g., as described herein, provide improvement in muscle activation which is effective at altering the biomechanical risk factors that indicate a higher risk for ACL injury. As such, devices and methods as described herein find use in training purposes to prevent ACL tears (see e.g., Bodor. Quadriceps protects the anterior cruciate ligament. Journal of Orthopaedic Research 19 (2001) 629-633).

Embodiments of the devices and methods find use in the fields of rehabilitation and pain mitigation associated with musculoskeletal injury and disease. Devices are designed to activate the mechanoreceptors of the somatosensory system to respond to a mechanical stimulus in a manner that elicits a functional response. Embodiments of the invention provide a low profile device that can be easily applied, can be worn in an unobtrusive manner and can be constructed at a reasonable cost.

Kits

Also provided are kits that at least include one or more devices, e.g., as described above, and which may be used according to the subject methods. The subject kits may include two or more, e.g., a plurality, three, four, five, eight, ten, etc., devices or other system components according to any of the embodiments described herein, or any combinations thereof. Kits may also include packaging, e.g., packaging for shipping the systems and/or devices without breaking.

In certain embodiments, the kits which are disclosed herein include instructions, such as instructions for using the subject devices and/or systems. The instructions are, in some aspects, recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging etc.). In other embodiments, the instructions are present as an electronic storage data file present on a suitable computer readable storage medium, e.g., Portable Flash drive, CD-ROM, diskette, etc. The instructions may take any form, including complete instructions for how to use the systems or devices or as a website address with which instructions posted on the world wide web may be accessed.

The following examples are offered by way of illustration and not by way of limitation.

EXPERIMENTAL

Figure 4A:
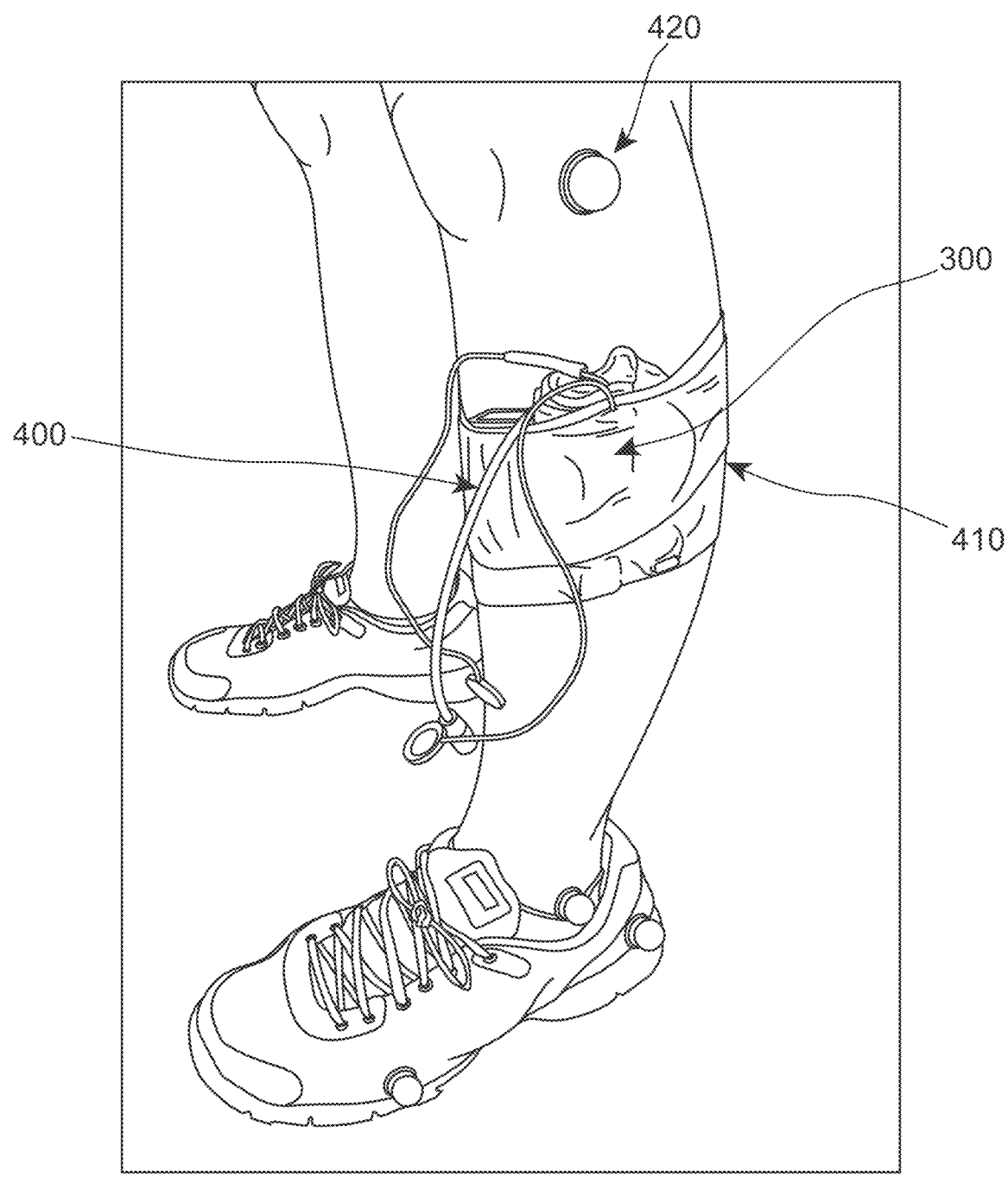
FIGS. 4A-4B show a device according to an embodiment of the invention that includes two active stimulus modules.
Figure 4B:
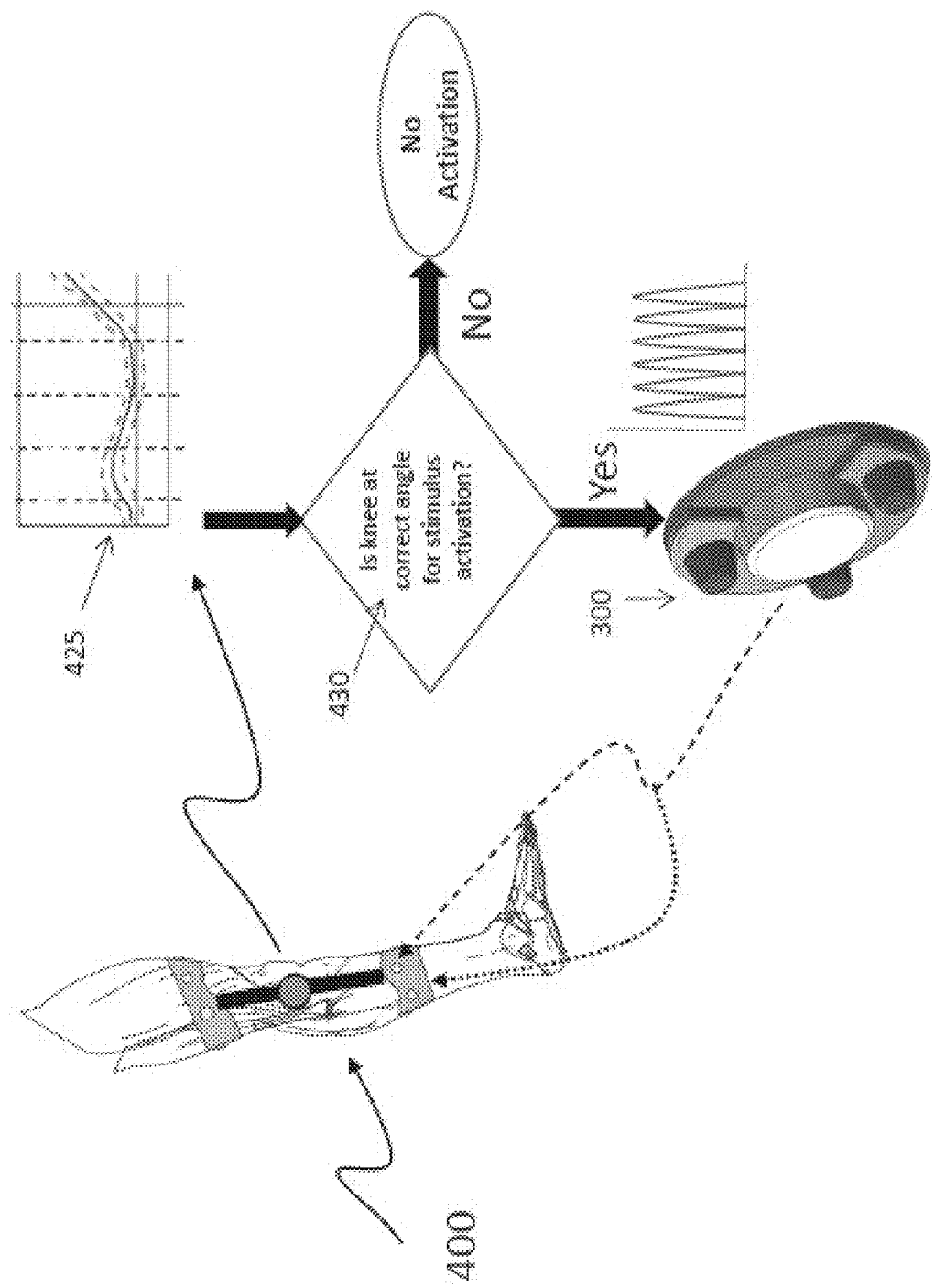

Two different prototypes were created to demonstrate the effects of vibratory and tactile cutaneous stimulation on activation of the mechanoreceptors of the somatosensory system to elicit a functional response. Prototype 1 employed a stimulation module 300 shown in FIG. 3 that included an integrated combination of a central vibratory component 310 surrounded circumferentially by four 3D printed tactile stimulation components 311, 312, 313 and 314. From stimulation module 300, vibratory stimulus may be applied via a vibration motor, with tactile stimulation applied using the 3D printed shape components placed around the vibration motor. The stimulation may be applied to a leg in either a constant or intermittent mode, as desired. Where an intermittent mode is employed, the duration of any given stimulus may vary, ranging in some instances between 0.2 and 2 s, such as 0.5 to 1 s, and the duration of any intervening non-stimulation period may also vary, ranging in some instances from 0.2 to 2 s, such as 0.5 to 1 s. The position of the vibration motor on the leg can be varied. The tactile stimulus can be removed to provide only vibratory stimulation, if desired. The stimulation module 300 is part of a device 400, portions of which are shown in FIG. 4A. The portion of device 400 is shown applied to a leg by an elastic band 410. A goniometer 420 is incorporated as the sensing module spanning the knee joint to allow calculation of knee flexion angle during walking, and subsequently timing of the gait cycle. A processor receives data from the goniometer to allow intermittent stimulation to be applied based on position in the gait cycle, determined from knee flexion angle, if desired. FIG. 4B provides a schematic of the operation of the operation of the device 400, and provides a flow chart illustrating algorithm employed by the processor in activating the stimulation module in response to received data from the goniometer. As illustrated in FIG. 4B, goniometer 420 produces knee flexion angle output data 425 which is input into processing module 430. Processing module 430 processes the input data and determines whether the knee is within a desired angle range for stimulation by determining whether the output angle from the goniometer falls within a predetermined range, e.g., −5 to 20 degrees (positive indicating knee flexion and negative indicating extension). If the knee angle is within the desired range, processor activates the stimulation module 300 as shown to vibrate. If the knee angle is not in the desired range, processor maintains the stimulation module in the inactive state without vibration.

Figure 5:
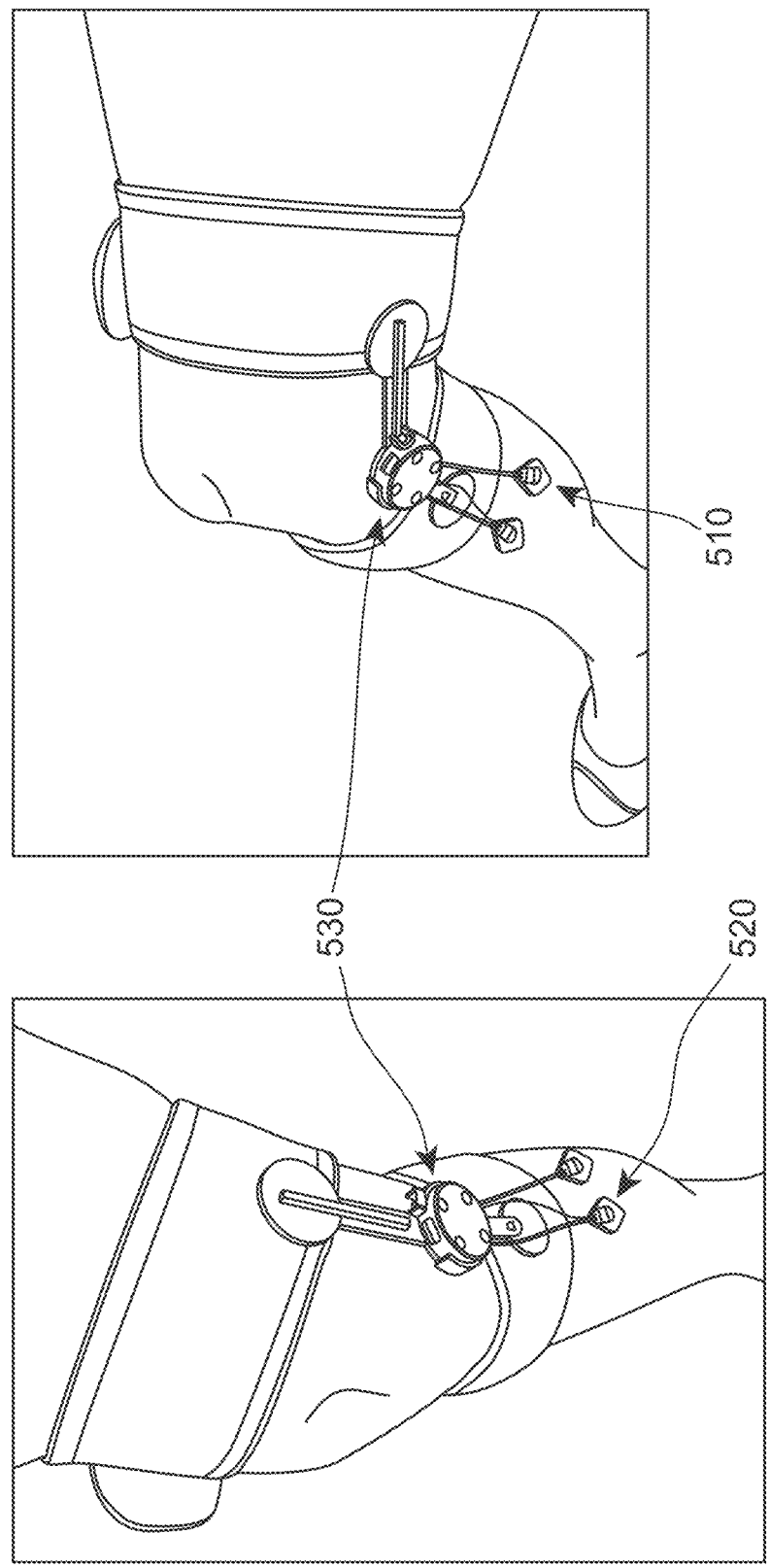
FIG. 5 shows a device according to an embodiment of the invention that includes two active stimulus modules, where the configuration differs from that shown in FIGS. 4A and 4B.

Prototype 2 is shown in FIG. 5 and includes two vibratory stimulus modules 510 and 520 applied to the leg. The vibratory stimulus modules include vibration motors that apply vibratory stimuli, and the position of the motors can be varied. As with Prototype 1, tactile stimulation can also be applied using 3D printed shapes placed around the vibration motor(s). A potentiometer 530 is incorporated as the sensing module spanning the knee joint to allow calculation of knee flexion angle during walking, and subsequently timing of the gait cycle. A processor (not shown) receives data from the potentiometer to allow intermittent stimulation to be applied based on position in the gait cycle, determined from knee flexion angle, if desired. The prototype is attached to the leg via Velcro straps on the thigh and shank. The prototype can operate in either constant or intermittent mode.

Notwithstanding the appended clauses, the disclosure is also defined by the following clauses:
1. A cutaneous stimulation device comprising:
   a cutaneous stimulation module configured to apply a tactile stimulus to a skin location; and
   a cutaneous association element configured to stably associate the module with the skin location.
2. The cutaneous stimulation device according to Clause 1, wherein the cutaneous stimulation module is a passive stimulation module.
3. The cutaneous stimulation device according to Clause 2, wherein the cutaneous stimulation module is configured to apply pressure to the skin location.
4. The cutaneous stimulation device according to any of Clauses 2 or 3, wherein the cutaneous stimulation module comprises a shaped object.
5. The cutaneous stimulation device according to Clause 4, wherein the shaped object comprises a three-dimensional printed object.
6. The cutaneous stimulation device according to Clause 1, wherein the cutaneous stimulation module is an active stimulation module.
7. The cutaneous stimulation device according to Clause 6, wherein the cutaneous stimulation module is configured to apply vibration to the skin location.
8. The cutaneous stimulation device according to Clause 7, wherein the cutaneous stimulation module comprises a vibratory element configured to apply vibration at a frequency ranging from 20 to 450 Hz.
9. The cutaneous stimulation device according to Clause 6, wherein the cutaneous stimulation module is configured to apply thermal modulation to the skin location.
10. The cutaneous stimulation device according to Clause 9, wherein the cutaneous stimulation module is configured to assume a temperature at a skin contact surface ranging from 5 to 45° C.
11. The cutaneous stimulation device according to any of the preceding clauses, wherein the cutaneous stimulation module is present on a device that comprises two or more cutaneous stimulus modules
12. The cutaneous stimulation device according to Clause 11, wherein the device comprises a passive stimulation module and an active stimulation module.
13. The cutaneous stimulation device according to Clause 12, wherein the passive stimulation module is configured to apply pressure to a skin location and the active stimulation module is configured to apply vibration to a skin location.
14. The cutaneous stimulation device according to any of Clauses 12 to 13, wherein the device comprises more passive stimulation modules than active stimulation modules.
15. A cutaneous stimulation device according to any of the preceding clauses, wherein the device further comprises:
   (a) a sensor configured to obtain physical data from the subject and output the obtained physical data to a processor; and
   (b) a processor configured to activate a cutaneous stimulation module in response to received output physical data from the sensor.
16. The cutaneous stimulation device according to Clause 15, wherein the physical data comprises motion data.
17. The cutaneous stimulation device according to Clause 15, wherein the physical data comprises orientation data.
18. The cutaneous stimulation device according to Clause 15, wherein the physical data comprises force data.
19. The cutaneous stimulation device according to Clause 15, wherein the sensor comprises a goniometer.
20. The cutaneous stimulation device according to any of the preceding clauses, wherein the cutaneous stimulation module is stably associated with a cutaneous association element.
21. The cutaneous stimulation device according to Clause 20, wherein the cutaneous associate element comprises an elastic band.
22. The cutaneous stimulation device according to Clause 20, wherein the cutaneous association element comprises an adhesive.
23. The cutaneous stimulation device according to Clause 22, wherein the adhesive is present on a skin association area of the cutaneous stimulation module or on a tape with which the cutaneous stimulation module is associated.
24. The cutaneous stimulation device according to any of the preceding clauses, wherein the skin location is present on a limb.
25. The cutaneous stimulation device according to Clause 18, wherein the limb is a leg.
26. A cutaneous stimulation module configured to apply a stimulus to a skin location of a subject, the cutaneous stimulation module comprising:
   (a) a sensor configured to obtain physical data from the subject and output the obtained physical data to a processor;
   (b) a stimulator configured to apply a stimulus to a skin location;
   (c) a processor configured to activate the stimulator in response to received output physical data from the sensor.
27. The cutaneous stimulation module according to Clause 26, wherein the stimulus comprises pressure.
28. The cutaneous stimulation module according to Clause 26, wherein the stimulus comprises temporal displacement.

29. The cutaneous stimulation module according to Clause 26, wherein the stimulus comprises vibration.
30. The cutaneous stimulation module according to Clause 26, wherein the stimulus comprises thermal modulation.
31. The cutaneous stimulation module according to Clause 30, wherein the thermal modulation comprises heat.
32. The cutaneous stimulation module according to any of Clauses 26 to 31, wherein the physical data comprises motion data.
33. The cutaneous stimulation module according to any of Clauses 26 to 31, wherein the physical data comprises orientation data.
34. The cutaneous stimulation module according to any of Clauses 26 to 31, wherein the physical data comprises force data.
35. The cutaneous stimulation module according to any of Clauses 26 to 34, wherein the cutaneous stimulation module is stably associated with a cutaneous association element.
36. The cutaneous stimulation module according to Clause 35, wherein the cutaneous associate element comprises an elastic band.
37. The cutaneous stimulation module according to Clause 35, wherein the cutaneous association element comprises an adhesive.
38. The cutaneous stimulation module according to Clause 37, wherein the adhesive is present on a skin association area of the cutaneous stimulation module or on a tape with which the cutaneous stimulation module is associated.
39. The cutaneous stimulation module according to any of the Clauses 26 to 38, wherein the skin location is present on a limb.
40. The cutaneous stimulation module according to Clause 39, wherein the limb is a leg.
41. The cutaneous stimulation module according to any of Clauses 26 to 40, wherein the cutaneous stimulation module is present on a device that comprises two or more cutaneous stimulus modules.
42. A cutaneous stimulation device, the device comprising:
    a connector; and
    two or more cutaneous stimulation modules stably associated with the connector, wherein at least one of the cutaneous stimulation modules comprises:
    (a) a sensor configured to obtain physical data from the subject and output the obtained physical data to a processor;
    (b) a stimulator configured to apply a stimulus to a skin location;
    (c) a processor configured to activate the stimulator in response to received output physical data from the sensor.
43. The cutaneous stimulation device according to Clause 42, wherein the connector comprises an elastic band.
44. The cutaneous stimulation device according to Clause 42, wherein the connector comprises an adhesive tape.
45. A cutaneous stimulation device, the device comprising:
    an elastic band configured to encircle a portion of a limb of a subject; and
    a passive stimulation module stably associated with the elastic band and configured to apply pressure to a skin location in response to dimensional modulation of the elastic band.
46. The cutaneous stimulation device according to Clause 45, wherein the limb is a leg.
47. The cutaneous stimulation device according to Clause 46, wherein the limb is an arm.
48. The cutaneous stimulation device according to any of Clauses 45 to 47, wherein the dimensional modulation comprises stretching of the elastic band.
49. The cutaneous stimulation device according to any of Clauses 45 to 48, wherein the passive stimulation module comprises a rigid skin contact surface.
50. The cutaneous stimulation device according to any of Clauses 45 to 49, wherein the devices comprises two or more passive stimulation modules.
51. A method of applying a stimulus to a skin location of a subject, the method comprising:
    stably associating a cutaneous stimulation module of a device according to any of Clauses 1 to 25 with the skin location; and
    maintaining the stably associated cutaneous stimulation module with the skin location in a manner sufficient to apply a stimulus to the skin location.
52. The method according to Clause 51, wherein the subject has a musculoskeletal condition.
53. The method according to Clause 52, wherein the method is a method is rehabilitating the subject.
54. The method according to Clauses 52 or 53, wherein the method is a method of mitigating pain experienced by the subject.
55. The method according to any of Clauses 52 to 54, wherein the musculoskeletal condition comprises an injury.
56. The method according to Clause 55, wherein the injury is a ligamentous injury.
57. The method according to Clause 56, wherein the ligamentous injury is an ACL injury.
58. The method according to Clauses 52 to 57, wherein the musculoskeletal condition is a disease.
59. The method according to Clause 58, wherein the disease is osteoarthritis.
60. The method according to Clause 58, wherein the disease is a degenerative joint condition.
61. The method according to Clauses 52 to 54, wherein the musculoskeletal condition is a result of a surgical procedure.
62. The method according to Clause 61, wherein the surgical procedure is a meniscectomy.
63. The method according to Clause 61, wherein the surgical procedure is an ACL reconstruction.
64. The method according to any of Clauses 51 to 63, wherein the subject is a mammal.
65. The method according to Clause 64, wherein the mammal is a human.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:
1. A method of mitigating knee pain experienced by a subject during ambulation, the method comprising:
    receiving gait cycle data during movement of a knee of the subject; and
    intermittently activating cutaneous stimulation modules in response to the received gait cycle data to activate mechanoreceptors of the subject to activate the somatosensory system of the subject and mitigate knee pain experienced by the subject during ambulation, wherein the cutaneous stimulation modules comprise:
a first vibratory cutaneous stimulation module stably associated with a thigh skin location of the subject; and
a second vibratory cutaneous stimulation module stably associated with a leg shank skin location of a subject,
and the method comprises activating the first and second cutaneous stimulation modules when a flexion angle of the knee ranges from −5 to 20 degrees.

2. The method according to claim 1, wherein the method comprises applying vibration with the first and second vibratory cutaneous stimulation modules at a frequency ranging from 20 to 450 Hz.

3. The method according to claim 1, wherein the method comprises activating the first and second vibratory cutaneous stimulation modules for a duration ranging from 0.2 to 2 sec.

4. The method according to claim 1, wherein the subject suffers from a musculoskeletal condition.

5. The method according to claim 4, wherein the musculoskeletal condition comprises an injury.

6. The method according to claim 5, wherein the injury is a ligamentous injury.

7. The method according to claim 6, wherein the ligamentous injury is an ACL injury.

8. The method according to claim 4, wherein the musculoskeletal condition is a disease.

9. The method according to claim 8, wherein the disease is osteoarthritis.

10. The method according to claim 8, wherein the disease is a degenerative joint condition.

11. The method according to claim 1, wherein the subject is a mammal.

12. The method according to claim 11, wherein the mammal is a human.

13. The method according to claim 1, wherein activating the somatosensory system does not require a conscious response from the subject.

* * * * *